(12) United States Patent
Suddaby (10) Patent No.: US 11,517,446 B2
(45) Date of Patent: Dec. 6, 2022

(54) EXPANDABLE INTERVERTEBRAL FUSION IMPLANT

(71) Applicant: Loubert S. Suddaby, Orchard Park, NY (US)

(72) Inventor: Loubert S. Suddaby, Orchard Park, NY (US)

(*) Notice: Subject to any disclaimer, the term of this patent is extended or adjusted under 35 U.S.C. 154(b) by 212 days.

(21) Appl. No.: 17/080,987

(22) Filed: Oct. 27, 2020

(65) Prior Publication Data

US 2022/0125598 A1    Apr. 28, 2022

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2002/3052* (2013.01); *A61F 2002/30153* (2013.01); *A61F 2002/30383* (2013.01); *A61F 2002/30525* (2013.01); *A61F 2002/30601* (2013.01); *A61F 2002/30784* (2013.01); *A61F 2310/00023* (2013.01)

(58) Field of Classification Search
CPC ................ A61F 2/44; A61F 2/30771; A61F 2002/30153; A61F 2002/30383; A61F 2002/3052; A61F 2002/30525; A61F 2002/30601; A61F 2002/30784; A61F 2310/00023
USPC ............................................ 623/17.11–17.16
See application file for complete search history.

(56) References Cited

U.S. PATENT DOCUMENTS

| | | | | |
|---|---|---|---|---|
| 6,159,244 A | * | 12/2000 | Suddaby | A61F 2/4611 606/247 |
| 6,174,334 B1 | * | 1/2001 | Suddaby | A61F 2/4455 623/17.11 |
| 6,562,074 B2 | * | 5/2003 | Gerbec | A61F 2/4611 623/17.15 |
| 7,094,257 B2 | * | 8/2006 | Mujwid | A61F 2/447 623/17.15 |
| 10,722,380 B1 | * | 7/2020 | Berry | A61F 2/4455 |
| 2010/0145456 A1 | * | 6/2010 | Simpson | A61F 2/4455 623/17.12 |
| 2011/0178599 A1 | * | 7/2011 | Brett | A61F 2/442 623/17.16 |
| 2013/0103156 A1 | * | 4/2013 | Packer | A61F 2/447 623/17.16 |
| 2017/0216045 A1 | * | 8/2017 | Dewey | A61F 2/4611 |
| 2018/0206999 A1 | * | 7/2018 | Suddaby | A61F 2/4455 |
| 2019/0110900 A1 | * | 4/2019 | Suddaby | A61F 2/4425 |
| 2021/0015626 A1 | * | 1/2021 | Suddaby | A61F 2/447 |
| 2021/0346167 A1 | * | 11/2021 | Dewey | A61F 2/4455 |
| 2021/0346170 A1 | * | 11/2021 | Dewey | A61F 2/447 |
| 2022/0125599 A1 | * | 4/2022 | Suddaby | A61F 2/4455 |

* cited by examiner

*Primary Examiner* — Jessica Weiss
(74) *Attorney, Agent, or Firm* — Harter Secrest & Emery LLP; Michael Nicholas Vranjes (57) ABSTRACT

An expandable intervertebral fusion implant, including an inferior component, including a first top surface, a first bottom surface, a first end, a second end, and a first hole including a first portion and a second portion, a superior component, including a second top surface, a second bottom surface, a third end, and a fourth end, and an expansion mechanism including a flexible shaft arranged in the first hole, the flexible shaft including a fifth end, a sixth end connected to the first bottom surface, and a first plurality of teeth.

20 Claims, 11 Drawing Sheets

EXPANDABLE INTERVERTEBRAL FUSION IMPLANT

FIELD

The present disclosure relates to orthopedic surgery, and more particularly to an expandable and deployable intervertebral fusion implant capable of being placed within an intervertebral disc space and expanded.

BACKGROUND

Figure 1:
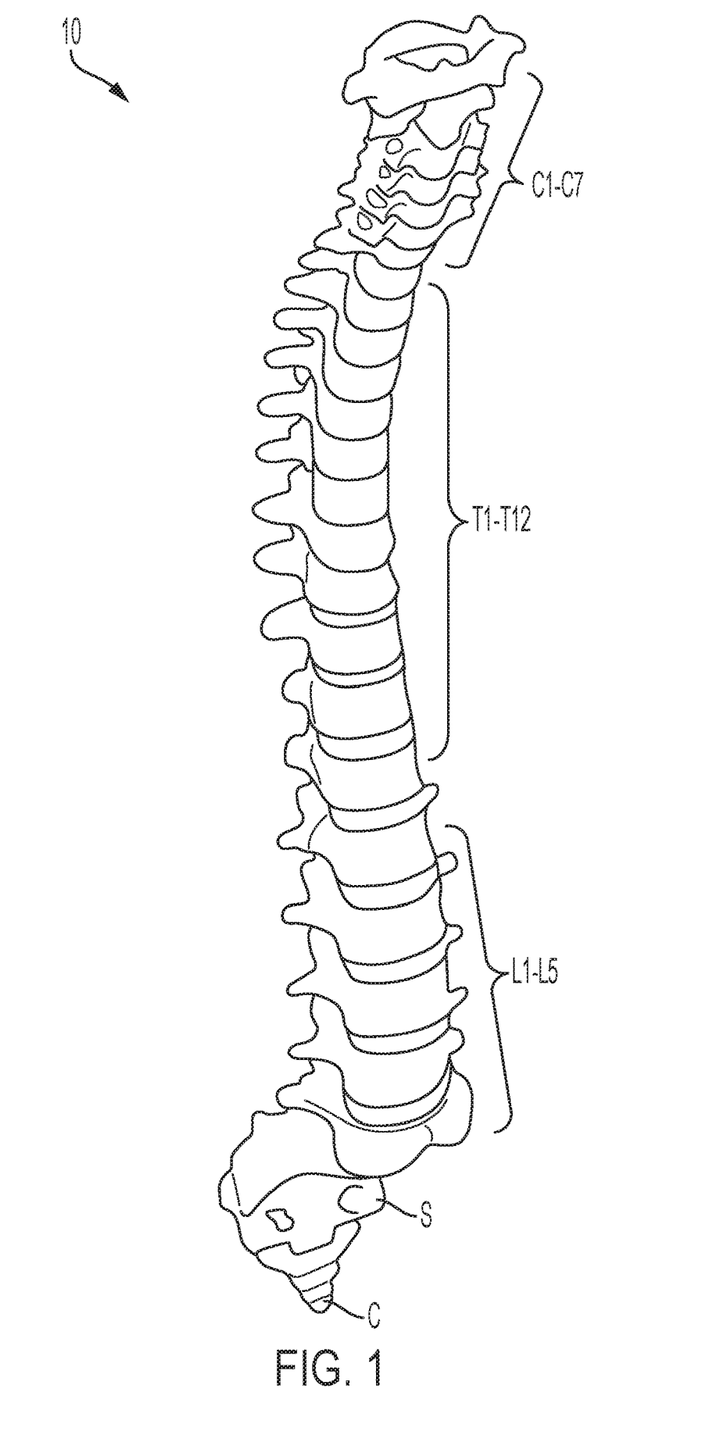
FIG. 1 is an anterior perspective view of a spinal column.

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae C1-C7 form the neck, support the head and neck, and allow nodding and shaking of the head. The thoracic vertebrae T1-T12 join with the ribs to form the rib cage. The five lumbar vertebrae L1-L5 carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information super-highway between the brain and the body. The nerves in the spinal cord branch off to form pairs of nerve roots that travel through the small openings between the vertebrae and the intervertebral foramens.

Figure 2:
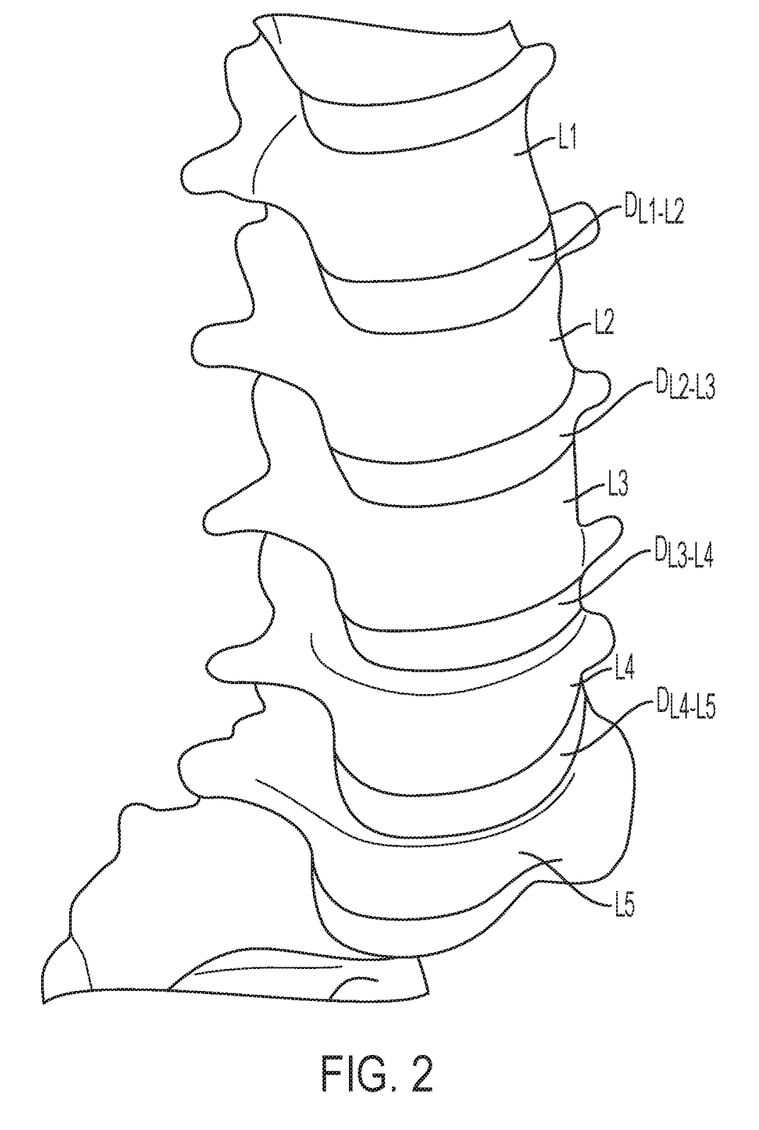
FIG. 2 is an anterior perspective view of the lumbar section of the spinal column shown in FIG. 1.
Figure 3:
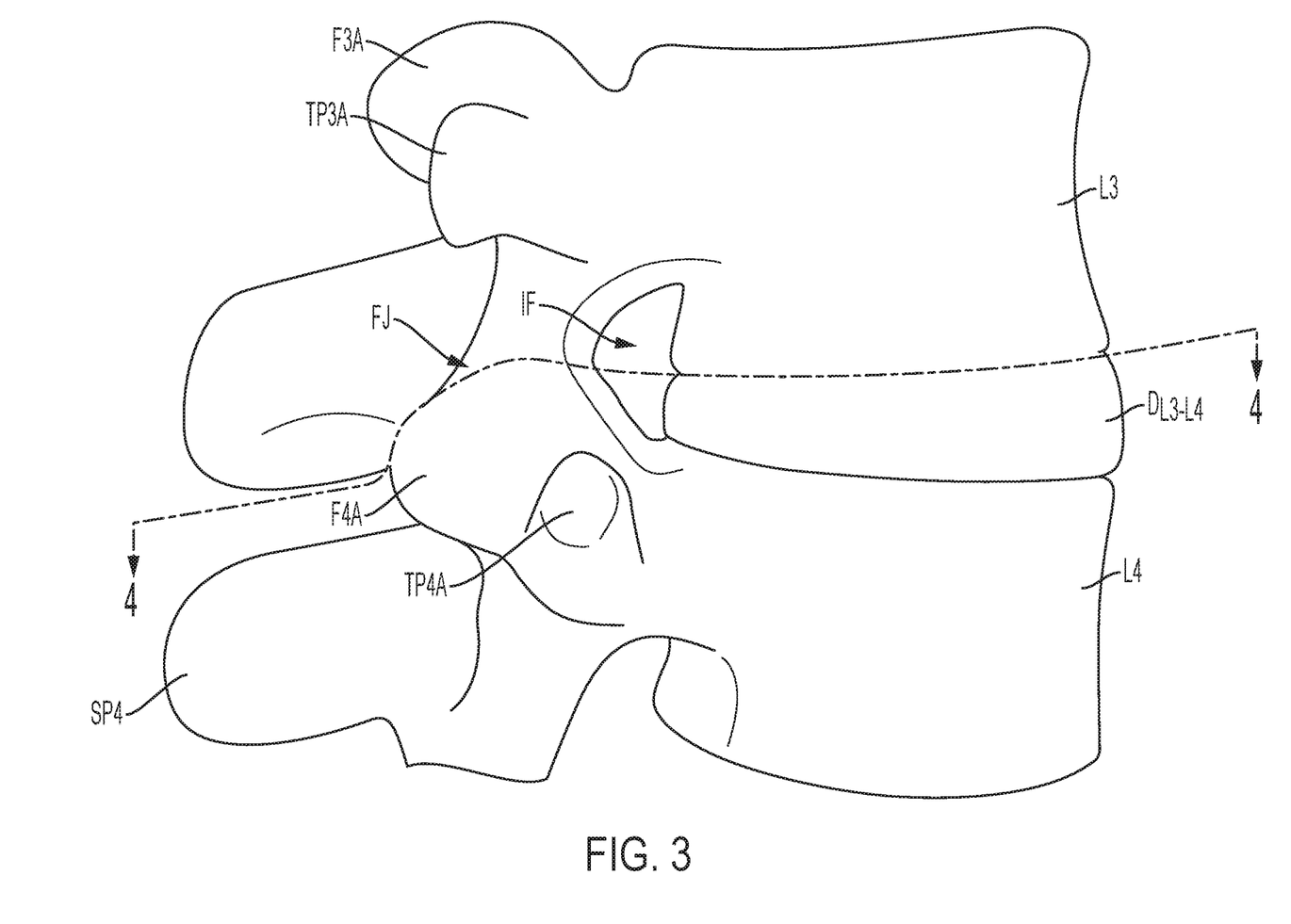
FIG. 3 is a lateral perspective view of two vertebrae, a disc, and related spinal anatomy.
Figure 4:
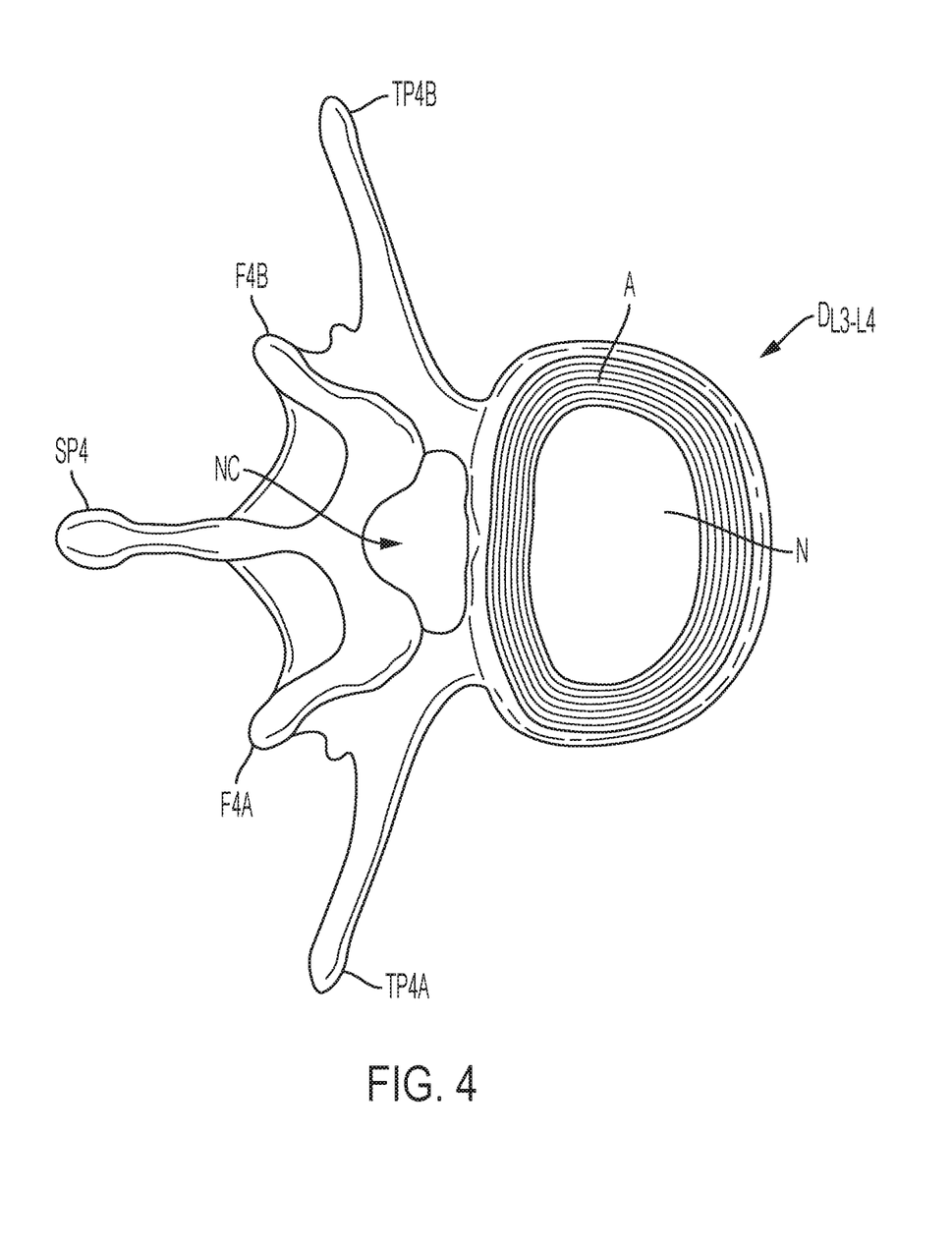
FIG. 4 is a top view of a section of the spinal column, taken generally along line 4-4 in FIG. 3.
Figure 5:
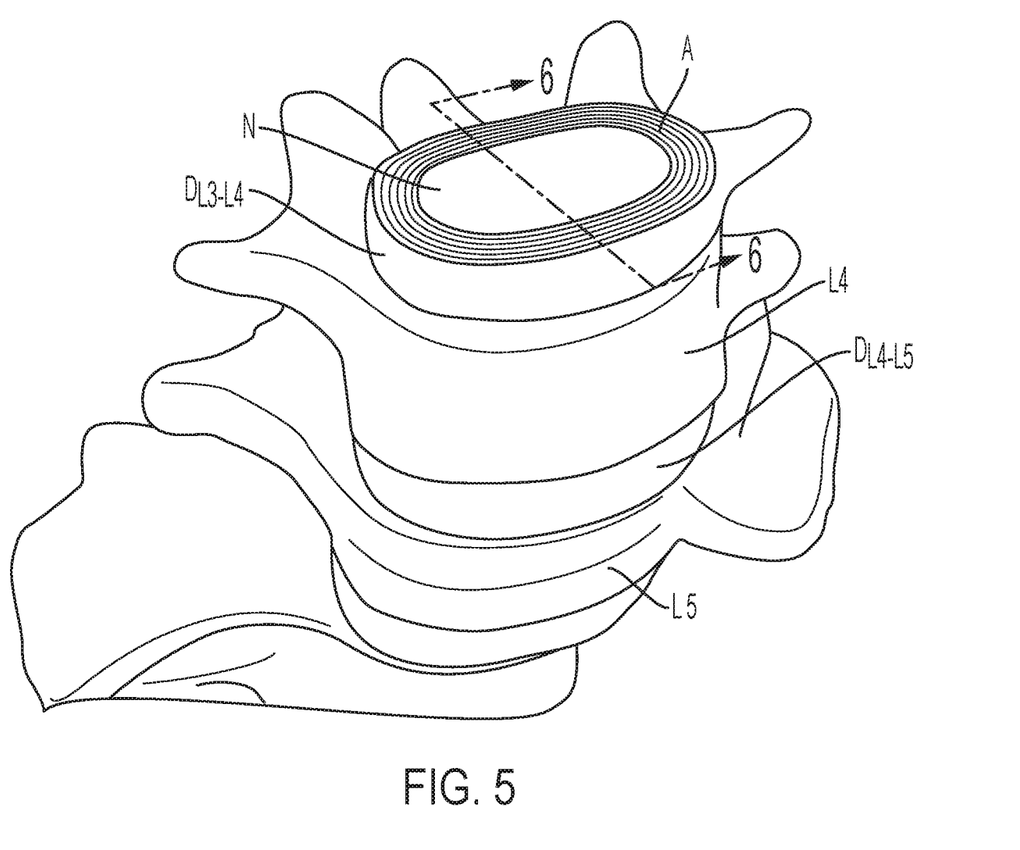
FIG. 5 is an enlarged anterior perspective view of the spinal column shown in FIG. 2, except with the top vertebra and all other structure above the top vertebra removed.
Figure 6:
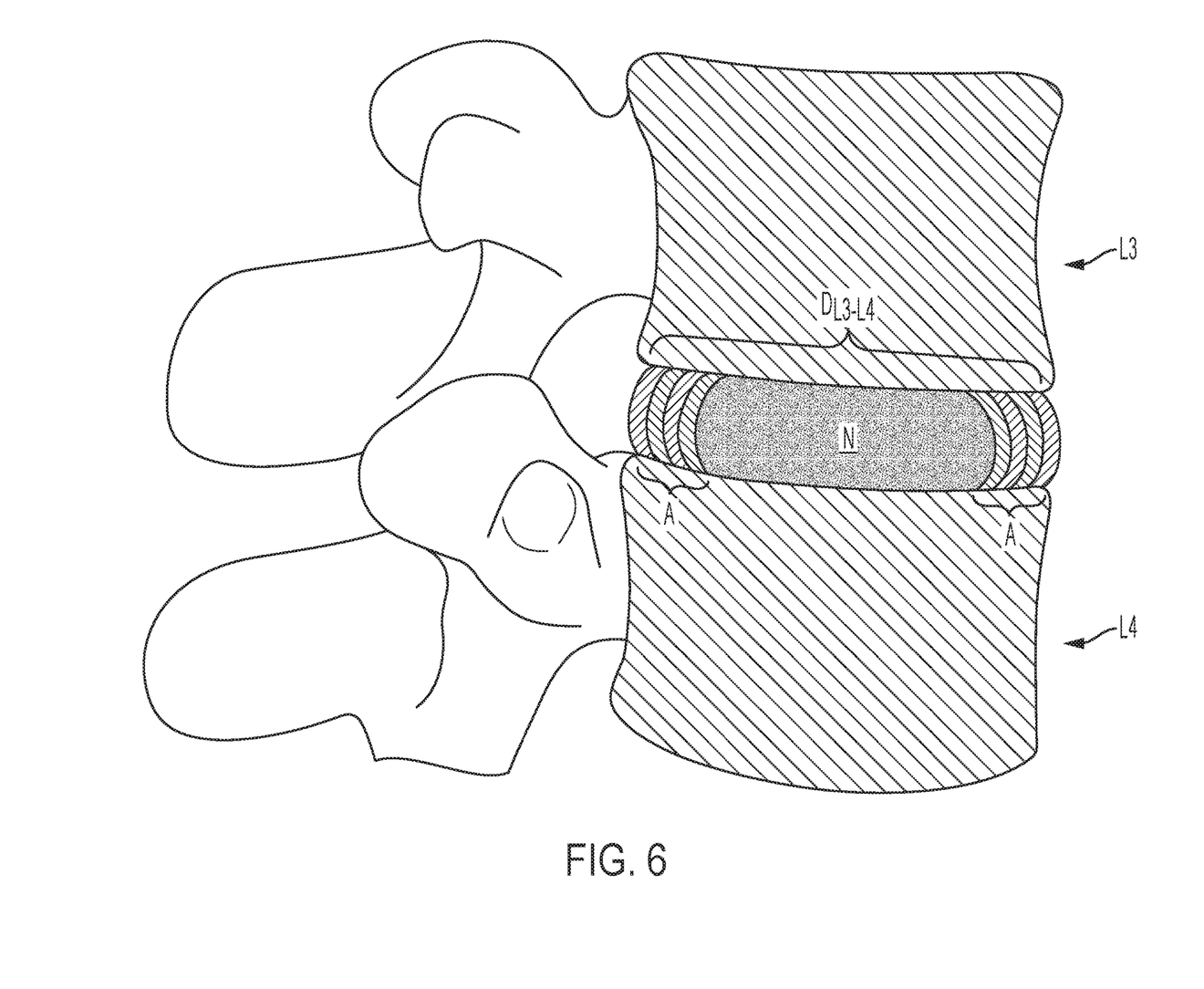
FIG. 6 is a partial cross-sectional view of the top and bottom vertebrae and disc, taken generally along line 6-6 in FIG. 5.

Various medical conditions require a surgeon to repair, remove and/or replace the aforementioned discs. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 (not shown) and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, taken generally along line 6-6, but with vertebra L3 in place atop disc $D_{L3-L4}$.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, five in the lower back or lumbar region, and five in the pelvic or sacral region, which are normally fused together to form the back part of the pelvis. This column of bones is critical for providing structural support for the entire body.

Between the vertebral bones themselves exist soft tissue structures, i.e., discs, composed of fibrous tissue and cartilage that are compressible and act as shock absorbers for sudden downward forces on the upright column. The discs allow the bones to move independently of each other, as well. The repetitive forces which act on these intervertebral discs during repetitive activities of bending, lifting, and twisting cause them to break down or degenerate over time.

Presumably, because of humans' upright posture their intervertebral discs have a high propensity to degenerate. Overt trauma or covert trauma, occurring in the course of repetitive activities, disproportionately affects the more highly mobile areas of the spine. Disruption of a disc's internal architecture leads to bulging, herniation, or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal movement.

The time-honored method of addressing the issues of neural irritation and instability resulting from severe disc damage has largely focused on removal of the damaged disc and fusing the adjacent vertebral elements together. Removal of the disc relieves the mechanical and chemical irritation of neural elements, while osseous union (i.e., bone knitting) solves the problem of stability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union. Intervertebral prosthesis in various forms has therefore been used to provide immediate stability and to protect and preserve an environment that fosters growth of the grafted bone such that a structurally significant bony fusion can occur.

Limitations of most present-day intervertebral implants are significant and revolve largely around the marked variation in the disc space height and shape that result from either biologic variability or pathologic change. For example, if a disc space is 20 mm in height, a circular implant bridging this gap requires a minimum diameter of 20 mm just to contact the end plate of the vertebral bone. Generally, end plate disruption must occur to allow a generous bony union, meaning that an additional 2-3 mm must be added on either side resulting in a final implant size of 24-26 mm. During implantation from an anterior approach (i.e., from the front of the body), excessive retraction (or pulling) is often required on the great blood vessels, which greatly enhances the risk of devastating complications such as vascular tears or thrombosis. On the other hand, during a posterior approach, large implant diameters may require excessive traction on neural elements for adequate placement, even if all posterior bony elements are removed. In some instances, an adequate implant size cannot be inserted posteriorly, particularly if there is a significant degree of distraction to obtain stability by tightening the annular ligamentous tension band. Compromising on implant size risks sub-optimal stability or a loose implant, which has a greater risk of migration within, or expulsion from, the disc space. The alternative of excessively retracting neural elements to facilitate a posterior implant application results in a neuropraxia at best and permanent neural damage at worst.

Thus, there is a long-felt need for an expandable and deployable intervertebral fusion implant capable of being placed within an intervertebral disc space and expanded.

SUMMARY

According to aspects illustrated herein, there is provided an expandable intervertebral fusion implant, comprising an inferior component, including a first top surface, a first bottom surface, a first end, a second end, and a first hole including a first portion and a second portion, a superior component, including a second top surface, a second bottom surface, a third end, and a fourth end, and an expansion mechanism including a flexible shaft arranged in the first hole, the flexible shaft including a fifth end, a sixth end connected to the first bottom surface, and a first plurality of teeth.

In some embodiments, the inferior component further comprises a second hole arranged adjacent to the first hole, and a worm comprising threading, the threading being engaged with the first plurality of teeth. In some embodiments, when the worm is rotated in a first circumferential direction, the flexible shaft is displaced in a first direction and the superior component is displaced in a second direction relative to the inferior component. In some embodiments, the first direction is perpendicular to the second direction. In some embodiments, the sixth end is pivotably connected to the first bottom surface. In some embodiments, the first portion is perpendicular to the second portion, and the flexible shaft is arranged in both the first portion and the second portion. In some embodiments, the flexible shaft comprises nickel titanium. In some embodiments, the expandable intervertebral fusion implant further comprises a sheath arranged around the flexible shaft proximate the sixth end. In some embodiments, the sheath is connected to the first bottom surface and the second top surface. In some embodiments, the sheath comprises a plurality of telescoping members. In some embodiments, the expandable intervertebral fusion implant further comprises a section extending from one of the inferior component and the superior component and a groove arranged in the other of the inferior component and the superior component, the section being engaged with the groove.

According to aspects illustrated herein, there is provided an expandable intervertebral fusion implant, comprising an inferior component, including a first top surface, a first bottom surface, a first end, a second end, and a first hole including a first portion and a second portion, a superior component, including a second top surface, a second bottom surface, a third end, a fourth end, and a second hole including a third portion and a fourth portion, a first flexible shaft arranged in the first hole, the second flexible shaft including a fifth end, a sixth end connected to the first bottom surface, and a first plurality of teeth, and a second flexible shaft arranged in the second hole, the second flexible shaft including, a seventh end, an eight end connected to the second top surface, and a second plurality of teeth.

In some embodiments, the inferior component further comprises a third hole arranged adjacent to the first hole, and a first worm comprising first threading, the first threading being engaged with the first plurality of teeth. In some embodiments, when the first worm is rotated in a first circumferential direction, the first flexible shaft is displaced in a first direction and the superior component is displaced in a second direction relative to the inferior component, the first direction being different than the second direction. In some embodiments, the superior component further comprises a fourth hole arranged adjacent to the second hole, and a second worm comprising second threading, the second threading being engaged with the second plurality of teeth. In some embodiments, when the second worm is rotated in a first circumferential direction, the first flexible shaft is displaced in a first direction and the inferior component is displaced in a second direction relative to the superior component, the first direction being different than the second direction. In some embodiments, the first portion is not aligned with the second portion and the first flexible shaft is arranged in both the first portion and the second portion, and the third portion is not aligned with the fourth portion and the second flexible shaft is arranged in both the third portion and the fourth portion. In some embodiments, the expandable intervertebral fusion implant further comprises a sheath arranged around the first flexible shaft proximate the sixth end, the sheath being fixedly secured to the first bottom surface and the second top surface. In some embodiments, the sheath comprises a plurality of telescoping members.

According to aspects illustrated herein, there is provided an expandable intervertebral fusion implant, comprising an inferior component including a hole arranged therein, the hole including a first portion and a second portion, the second portion being unaligned with the first portion, a superior component displaceable relative to the inferior component, a flexible shaft slidably engaged in the first portion and the second portion, the flexible shaft including a first end, a second end pivotably connected to the superior component, and a plurality of teeth, and a worm arranged in the inferior component, the worm including threading engaged with the plurality of teeth.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be understood that use of "or" in the present application is with respect to a "non-exclusive" arrangement, unless stated otherwise. For example, when saying that "item x is A or B," it is understood that this can mean one of the following: (1) item x is only one or the other of A and B; (2) item x is both A and B. Alternately stated, the word "or" is not used to define an "exclusive or" arrangement. For example, an "exclusive or" arrangement for the statement "item x is A or B" would require that x can be only one of A and B. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Moreover, as used herein, the phrases "comprises at least one of" and "comprising at least one of" in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" is used herein. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

By "non-rotatably connected" elements, we mean that: the elements are connected so that whenever one of the elements rotate, all the elements rotate; and, relative rotation between the elements is not possible. Radial and/or axial movement of non-rotatably connected elements with respect to each other is possible, but not required. By "rotatably connected" elements, we mean that: the elements are rotatable with respect to each other; and, whenever one element is displaced radially and/or axially, all the elements are displaced radially and/or axially.

Adverting now to the figures, and as described previously, FIGS. 1-6 depict various parts and sections of spinal anatomy.

Figure 7A:
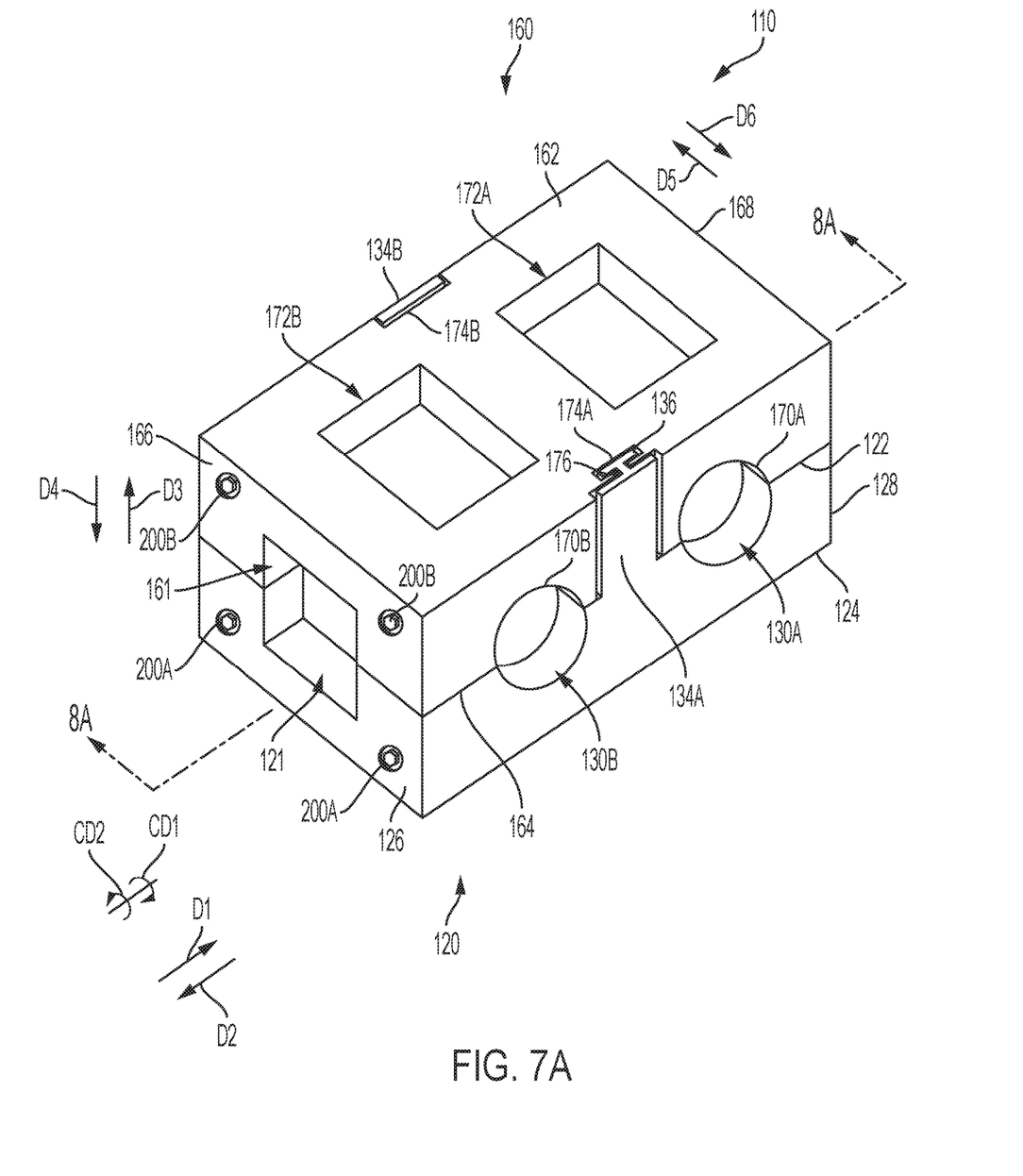
FIG. 7A is a front perspective view of an expandable intervertebral fusion implant, in a collapsed state.
Figure 7B:
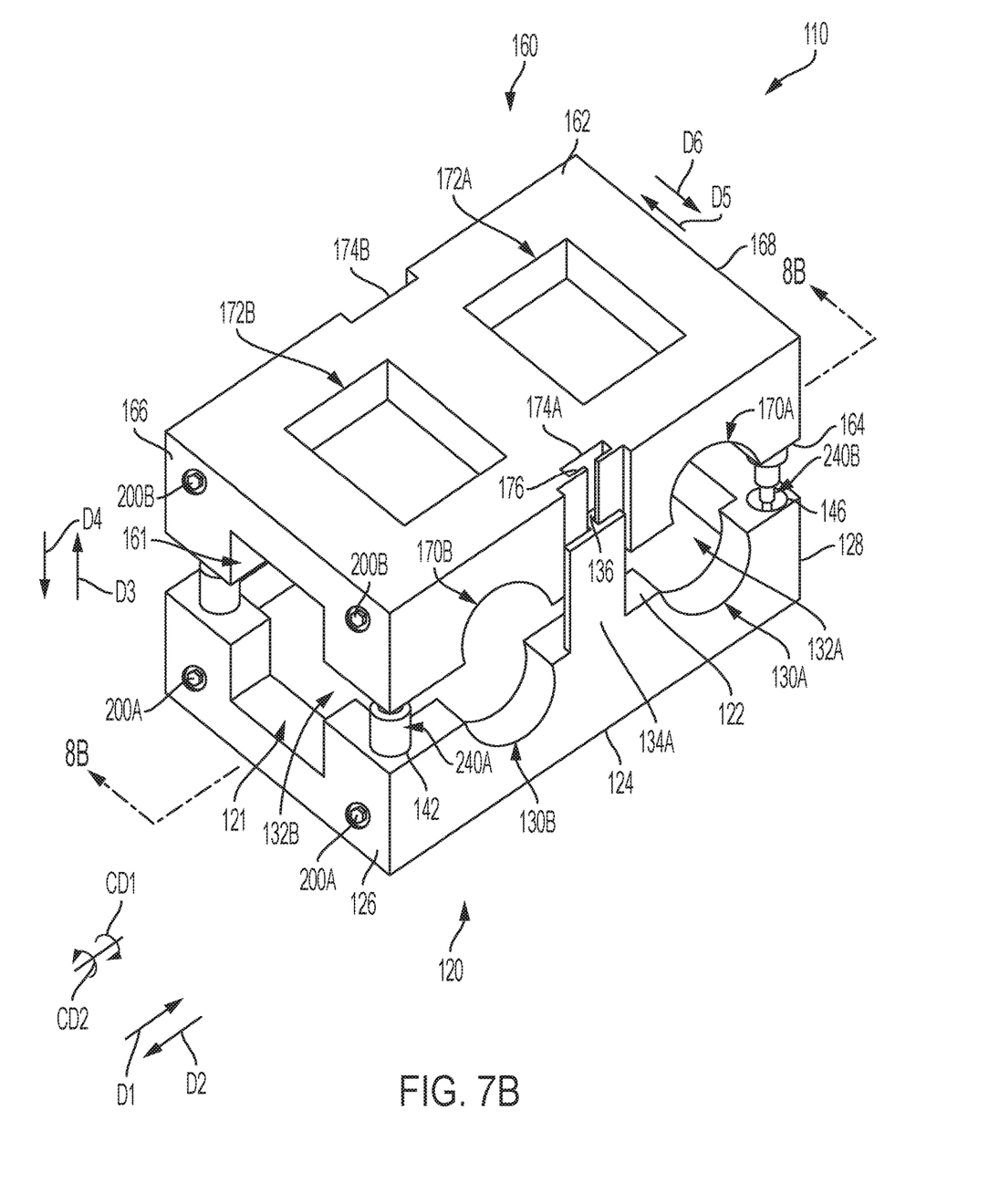
FIG. 7B is a front perspective view of the expandable intervertebral fusion implant shown in FIG. 7A, in an expanded state.
Figure 8A:
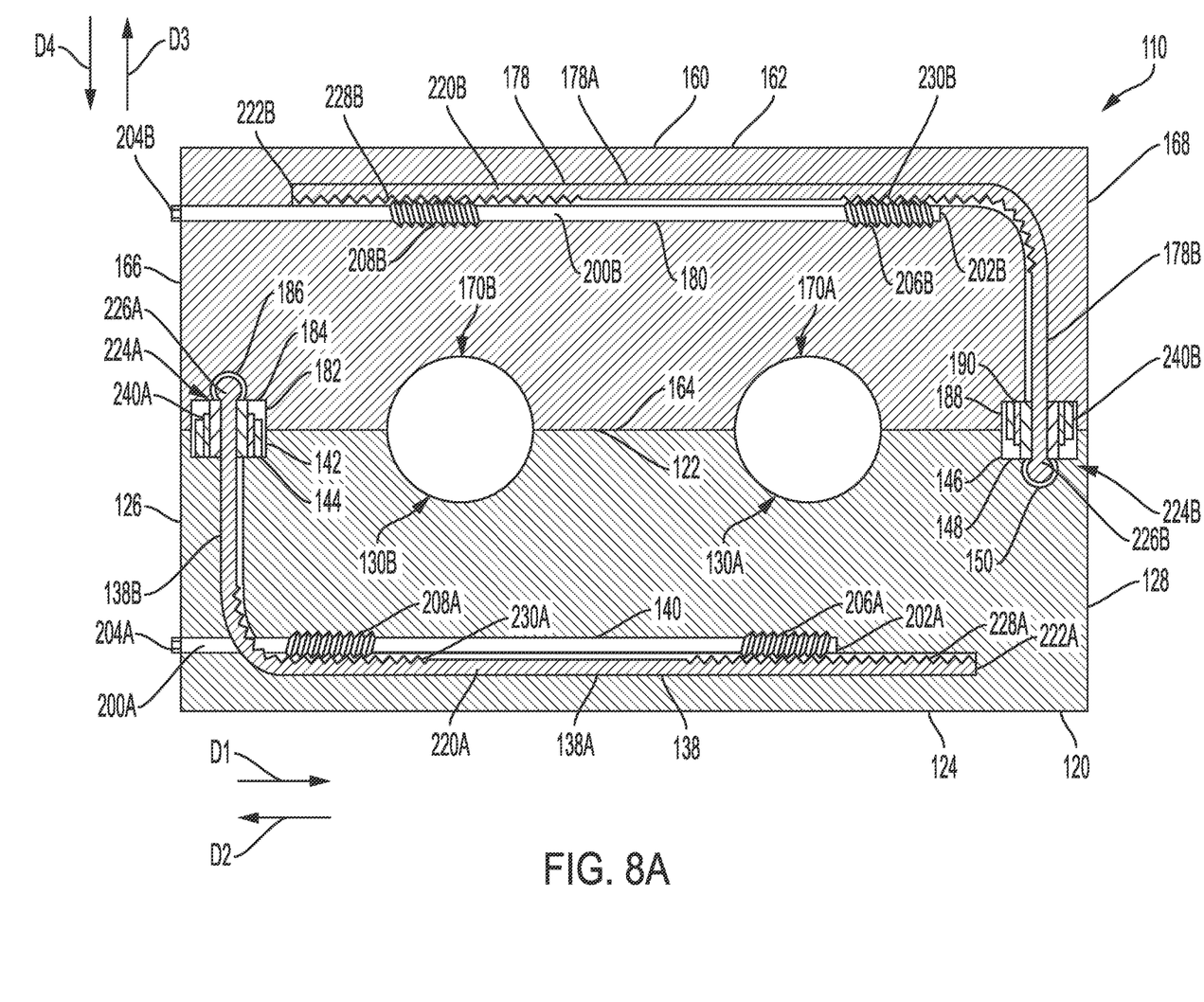
FIG. 8A is a cross-sectional view of the expandable intervertebral fusion implant taken generally along line 8A-8A in FIG. 7A.
Figure 8B:
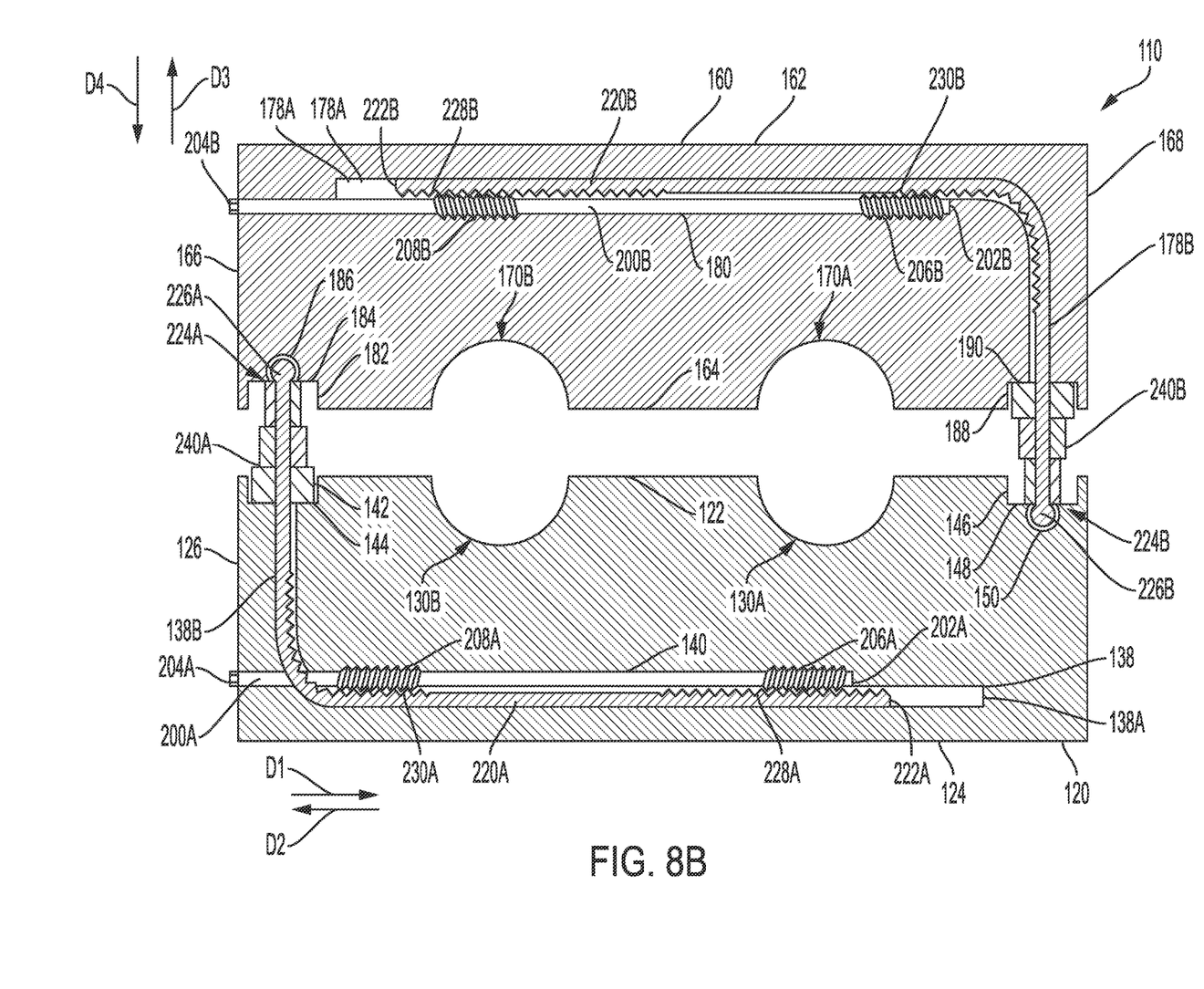
FIG. 8B is a cross-sectional view of the expandable intervertebral fusion implant taken generally along line 8B-8B in FIG. 7B; and, FIG. 9 is an anterior perspective view of a spinal column including the expandable intervertebral fusion implant shown in FIG. 7A, in the expanded state.

FIG. 7A is a front perspective view of expandable intervertebral fusion implant 110, in a collapsed state. FIG. 7B is a front perspective view of expandable intervertebral fusion implant 110, in an expanded state. FIG. 8A is a cross-sectional view of expandable intervertebral fusion implant 110 taken generally along line 8A-8A in FIG. 7A. FIG. 8B is a cross-sectional view of expandable intervertebral fusion implant 110 taken generally along line 8B-8B.

Expandable intervertebral fusion implant 110 generally comprises inferior component 120, superior component 160, and at least one expansion mechanism, for example, a worm drive comprising worm 200A and shaft 220A. The following description should be read in view of FIGS. 7A-8B.

Inferior component 120 comprises top surface 122, bottom surface 124, end 126, and end 128. Top surface 122 is an interior surface of expandable intervertebral fusion implant 110 that generally faces superior component 160 and is operatively arranged to engage and/or abut against surface 164. Bottom surface 124 is an exterior surface of expandable intervertebral fusion implant 110 that generally faces away from superior component 160 and is operatively arranged to engage and/or abut against a vertebra, as will be described in greater detail below. In some embodiments, surface 122 is arranged parallel to surface 124. In some embodiments, surface 122 is arranged nonparallel to surface 124.

In some embodiments, inferior component 120 further comprises one or more holes. For example, inferior component 120 comprises hole 121, which extends from end 126 to hole 128. Hole 121 extends from surface 122 in direction D4. Inferior component 120 comprises holes 130A and 130B, which extend through inferior component 120 in direction D5. Holes 130A-B extend from surface 122 in direction D4. Inferior component 120 comprises holes 132A and 132B (see FIG. 7B), which extend from surface 122 to surface 124. Holes 121, 130A-B, and 132A-B are operatively arranged to allow bone fusion material, which may be injected within expandable intervertebral fusion implant 110 once implanted within a spinal column, to engage adjacent vertebra thereby encouraging bony fusion. As such, it should be appreciated that any number of holes of any number of geometric shapes can be arranged in inferior component 120.

Inferior component 120 further comprises at least one section, for example section 134A and section 134B, which extends vertically from surface 122 in direction D3. Sections 134A and 134B are operatively arranged to slidingly and pivotably engage grooves 174A and 174B, respectively, to maintain alignment of inferior component 120 and superior component 160 in directions D1 and D2 while still allowing superior component 160 and inferior component 120 to pivot with respect to each other. In some embodiments, section 134A comprises tongue 136 extending in direction D5 therefrom. In some embodiments, section 134B comprises a tongue.

Inferior component 120 further comprises one or more holes, for example holes 142 and 146. Hole 142 is generally arranged proximate end 126 and extends from surface 122 in direction D4. Hole 142 comprises surface 144 and engages shaft 220A and sheath 240A, as will be described in greater detail below. In some embodiments, hole 142 is tapered toward surface 144. Hole 146 is generally arranged proximate end 128 and extends from surface 122 in direction D4. Hole 146 comprises surface 148 and engages shaft 220B and sheath 240B, as will be described in greater detail below. In some embodiments, hole 146 is tapered toward surface 148. In some embodiments, hole 146 further comprises socket 150 arranged proximate (or in) surface 148. Socket 150 is operatively arranged to engage ball 226B of shaft 220B to expand and contract expandable intervertebral fusion implant 110.

Inferior component 120 further comprises hole 138 and hole 140. Hole 138 comprises portion 138A and portion 138B. In some embodiments, portion 138A is substantially parallel to surface 124 and portion 138B is substantially parallel to end 126, meaning portion 138B is substantially perpendicular to portion 138A. In some embodiments, portion 138A is non-parallel to surface 124 and portion 138B is nonparallel to end 126. In some embodiments, portion 138B is not perpendicular to portion 138A. Shaft 220A is operatively arranged to be slidingly engaged in hole 138. Hole 140 is arranged adjacent to hole 138. Specifically, hole 140 extends from end 126 in direction D1 and is arranged adjacent to portion 138A. Worm 200A is operatively arranged to be rotatably connected in hole 140. As such, worm 200A is capable of rotational displacement in circumferential directions CD1 and CD2 relative to inferior component 120 but cannot displace axially in directions D1 and D2 relative to inferior component 120. As will be described in greater detail below, the arrangement of holes 138 and 140 is such that worm 200A, specifically threading 206A and 208A, is capable of engaging with shaft 220A, specifically teeth 228A and 230A, respectively, to displace shaft 220A within hole 138 and expand and contract expandable intervertebral fusion implant 110.

Superior component 160 comprises top surface 162, bottom surface 164, end 166, and end 168. Top surface 162 is an exterior surface of expandable intervertebral fusion implant 110 that generally faces away from inferior component 120 and is operatively arranged to engage and/or abut against a vertebra, as will be described in greater detail below. Bottom surface 164 is an interior surface of expandable intervertebral fusion implant 110 that generally faces inferior component 120 and is operatively arranged to engage and/or abut against surface 122, as will be described in greater detail below. In some embodiments, surface 162 is arranged parallel to surface 164. In some embodiments, surface 162 is arranged nonparallel to surface 164.

In some embodiments, superior component 160 further comprises one or more holes. For example, superior component 160 comprises hole 161, which extends from end 166 to hole 168. Hole 161 extends from surface 164 in direction D3. Superior component 160 comprises holes 170A and 170B, which extend through superior component 160 in direction D5. Holes 170A-B extend from surface 162 in direction D3. Superior component 160 comprises holes 172A and 172B, which extend from surface 162 to surface 164. Holes 161, 170A-B, and 172A-B are operatively arranged to allow bone fusion material, which may be injected within expandable intervertebral fusion implant 110 once implanted within a spinal column, to engage adjacent vertebra thereby encouraging bony fusion. As such, it should be appreciated that any number of holes of any number of geometric shapes can be arranged in superior component 160.

Superior component 160 further comprises at least one groove, for example groove 174A and section 174B, which extends from surface 162 to surface 164. Grooves 174A and 174B are operatively arranged to slidingly and pivotably engage sections 134A and 134B, respectively, to maintain alignment of superior component 160 and inferior component 120 in directions D1 and D2 while still allowing superior component 160 and inferior component 120 to pivot with respect to each other. In some embodiments, groove 174A comprises channel 176. Groove 174A comprises a first width and channel 176 comprises a second width, the second width being less than the first width. Such arrangement allows tongue 136 to engage groove 174A such that superior component can displace in direction D3 and direction D4 relative to section 134A but cannot displace in direction D5 and direction D6, or direction D1 or direction D2, relative to section 134A and thus inferior component 120.

Superior component 160 further comprises one or more holes, for example holes 182 and 188. Hole 182 is generally arranged proximate end 166 and extends from surface 164 in direction D3. Hole 182 comprises surface 184 and engages shaft 220A and sheath 240A, as will be described in greater detail below. In some embodiments, hole 182 is tapered toward surface 184. In some embodiments, hole 182 further comprises socket 186 arranged proximate (or in) surface 184. Socket 186 is operatively arranged to engage ball 226A of shaft 220A to expand and contract expandable intervertebral fusion implant 110. Hole 188 is generally arranged proximate end 168 and extends from surface 164 in direction D3. Hole 188 comprises surface 190 and engages shaft 220B and sheath 240B, as will be described in greater detail below. In some embodiments, hole 188 is tapered toward surface 190.

Superior component 160 further comprises hole 178 and hole 180. Hole 178 comprises portion 178A and portion 178B. In some embodiments, portion 178A is substantially parallel to surface 162 and portion 178B is substantially parallel to end 168, meaning portion 178B is substantially perpendicular to portion 178A. In some embodiments, portion 178A is non-parallel to surface 162 and portion 178B is nonparallel to end 168. In some embodiments, portion 178B is not perpendicular to portion 178A. Shaft 220B is operatively arranged to be slidingly engaged in hole 178. Hole 180 is arranged adjacent to hole 178. Specifically, hole 180 extends from end 166 in direction D1 and is arranged adjacent to portion 178A. Worm 200B is operatively arranged to be rotatably connected in hole 180. As such, worm 200B is capable of rotational displacement in circumferential directions CD1 and CD2 relative to superior component 160 but cannot displace axially in directions D1 and D2 relative to inferior component 120. As will be described in greater detail below, the arrangement of holes 178 and 180 is such that worm 200B, specifically threading 206B and 208B, is capable of engaging with shaft 220B, specifically teeth 228B and 230B, respectively, to displace shaft 220B within hole 178 and expand and contract expandable intervertebral fusion implant 110.

Worm 200A is generally a cylinder or rod operatively arranged to rotatably engage hole 140. Worm 200A comprises end 202A, end 204A, and threading between ends 202A and 204A. In some embodiments, worm 200A comprises threading 206A proximate or at end 202A and threading 208A proximate end 204A. In some embodiments, the entirety of worm 200A is threaded. Worm 200A is capable of displacing circumferentially with respect to inferior component 120. Worm 200A is not capable of displacing axially, in directions D1 and D2, with respect to inferior component 120. In some embodiments, end 204A comprises a head arranged to be engaged by a tool in order to rotate worm 200A. Such head may comprise any drive type suitable for rotating worm 200A, for example, Phillips and Frearson, slotted, combination, socked, internal hex, Allen, torx, external hex, etc. As worm 200A is rotated, in circumferential directions CD1 or CD2, threading 206A and/or threading 208A engages teeth 228A and/or teeth 230A, respectively, to displace shaft 220A within hole 138.

Shaft or rack 220A is a flexible element that is slidably engaged with hole 138. Shaft 220A comprises end 222A, end 224A, and teeth arranged between ends 222A and 224A. In some embodiments, shaft 220A comprises teeth 228A proximate or at end 222A and teeth 230A arranged generally proximate end 224A. In some embodiments, the entirety of shaft 220A comprises teeth. End 224A is connected to superior component 160. In some embodiments, end 224A comprises ball 226A which is pivotably connected to socket 186 (i.e., a ball and socket joint). Such connection allows pivotably displacement between superior component 160 and end 224A. Shaft 220A is capable of displacing within hole 138. Specifically, within portion 138A shaft 220A is capable of displacing in directions D1 and D2 relative to inferior component 120 and within portion 138B shaft 220A is capable of displacing in directions D3 and D4 relative to inferior component 120. In some embodiments, shaft 220A comprises nickel titanium, also known as Nitinol, which is a metal alloy exhibiting the shape memory effect and superelasticity. The elasticity and/or flexibility of shaft 220A allows for the displacement of a first part of shaft 220A in a first direction (e.g., D2) to result in the displacement of a second part of shaft 220A to occur in a second direction (e.g., D3). The engagement of worm 200A and shaft 220A operates similar to a worm drive, wherein rotational displacement of worm 200A causes linear displacement of shaft 220A. As such, when worm 200A is rotated in a first rotational direction, shaft 220A is displaced within hole 138 such that end 224A and superior component 160 are displaced in direction D3 relative to inferior component 120, expanding expandable intervertebral fusion implant 110. When worm 200A is rotated in a second rotational direction, opposite the first rotational direction, shaft 220A is displaced within hole 138 such that end 224A and superior component 160 are displaced in direction D4 relative to inferior component 120, contracting expandable intervertebral fusion implant 110. In some embodiments, shaft 220A and hole 138 comprise a noncircular cross-sectional geometry (e.g., square, triangular, rectangular, ellipsoidal, trapezoidal, etc.) such that shaft 220A does not rotate within hole 138. Such geometry may be implemented in order to maintain engagement of threading 206A and 208A with teeth 228A and 230A, respectively.

In some embodiments, and as best shown in FIGS. 8A-8B, expandable intervertebral fusion implant 110 further comprises sheath 240A. Sheath 240A is arranged around shaft 220A proximate end 224A. In some embodiments, sheath 240A comprises a plurality of telescopingly engaged segments, with a first segment being connected to surface 144 and a second segment being connected to surface 184. As end 224A and superior component 160 is displaced in direction D3 relative to inferior component 120, sheath 240A is elongated in the vertical direction thereby protecting shaft 220A, hole 138, and socket 186 from ingrowth of foreign materials (e.g., tissue, bone fusion material, etc.).

Worm 200B is generally a cylinder or rod operatively arranged to rotatably engage hole 180. Worm 200B comprises end 202B, end 204B, and threading between ends 202B and 204B. In some embodiments, worm 200B comprises threading 206B proximate or at end 202B and threading 208B proximate end 204B. In some embodiments, the entirety of worm 200B is threaded. Worm 200B is capable of displacing circumferentially, in circumferential directions CD1 and CD2, with respect to superior component 160. Worm 200B is not capable of displacing axially, in directions D1 and D2, with respect to superior component 160. In some embodiments, end 204B comprises a head arranged to be engaged by a tool in order to rotate worm 200B. Such head may comprise any drive type suitable for rotating worm 200B, for example, Phillips and Frearson, slotted, combination, socked, internal hex, Allen, torx, external hex, etc. As worm 200B is rotated, threading 206B and/or threading 208B engages teeth 230B and/or teeth 228B, respectively, to displace shaft 220B within hole 178.

Shaft or rack 220B is a flexible element that is slidably engaged with hole 178. Shaft 220B comprises end 222B, end 224B, and teeth arranged between ends 222B and 224B. In some embodiments, shaft 220B comprises teeth 228B proximate or at end 222B and teeth 230B arranged generally proximate end 224B. In some embodiments, the entirety of shaft 220B comprises teeth. End 224B is connected to inferior component 120. In some embodiments, end 224B comprises ball 226B which is pivotably connected to socket 150 (i.e., a ball and socket joint). Such connection allows pivotably displacement between inferior component 120 and end 224B. Shaft 220B is capable of displacing within hole 178. Specifically, within portion 178A shaft 220B is capable of displacing in directions D1 and D2 relative to superior component 160 and within portion 178B shaft 220B is capable of displacing in directions D3 and D4 relative to superior component 160. In some embodiments, shaft 220B comprises nickel titanium, also known as Nitinol, which is a metal alloy exhibiting the shape memory effect and super-elasticity. The elasticity and/or flexibility of shaft 220B allows for the displacement of a first part of shaft 220B in a first direction (e.g., D1) to result in the displacement of a second part of shaft 220B to occur in a second direction (e.g., D4). The engagement of worm 200B and shaft 220B operates similar to a worm drive, wherein rotational displacement of worm 200B causes linear displacement of shaft 220B. As such, when worm 200B is rotated in a first rotational direction, shaft 220B is displaced within hole 178 such that end 224B and inferior component 120 are displaced in direction D4 relative to superior component 160, expanding expandable intervertebral fusion implant 110. When worm 200B is rotated in a second rotational direction, opposite the first rotational direction, shaft 220B is displaced within hole 178 such that end 224B and inferior component 120 are displaced in direction D3 relative to superior component 160, contracting expandable intervertebral fusion implant 110. In some embodiments, shaft 220B and hole 178 comprise a noncircular cross-sectional geometry (e.g., square, triangular, rectangular, ellipsoidal, trapezoidal, etc.) such that shaft 220B does not rotate within hole 178. Such geometry may be implemented in order to maintain engagement of threading 206B and 208B with teeth 230B and 228B, respectively.

In some embodiments, and as best shown in FIGS. 8A-8B, expandable intervertebral fusion implant 110 further comprises sheath 240B. Sheath 240B is arranged around shaft 220B proximate end 224B. In some embodiments, sheath 240B comprises a plurality of telescopingly engaged segments, with a first segment being connected to surface 148 and a second segment being connected to surface 190. As end 224B and inferior component 120 is displaced in direction D4 relative to superior component 160, sheath 240B is elongated in the vertical direction thereby protecting shaft 220B, hole 178, and socket 150 from ingrowth of foreign materials (e.g., tissue, bone fusion material, etc.).

It should be appreciated that in some embodiments, expandable intervertebral implant 110 comprises one or more expansion mechanisms, for example, four worm drives and four shafts. Specifically, and as shown, inferior component 120 comprises two worms 200A and two shafts 220A engaged with worms 200A, and superior component 160 comprises two worms 200B and two shafts 220B engaged with worms 200B. The arrangement of the expansion mechanisms as well as the pivotable connection of the shafts to the inferior/superior components (i.e., the ball and socket joints) allows for a user to individually expand and contract each corner of expandable intervertebral implant 110 to the desired height. In other words, surface 162 need not be parallel to surface 124, which allows for a more custom expansion of expandable intervertebral implant 110.

Figure 9:
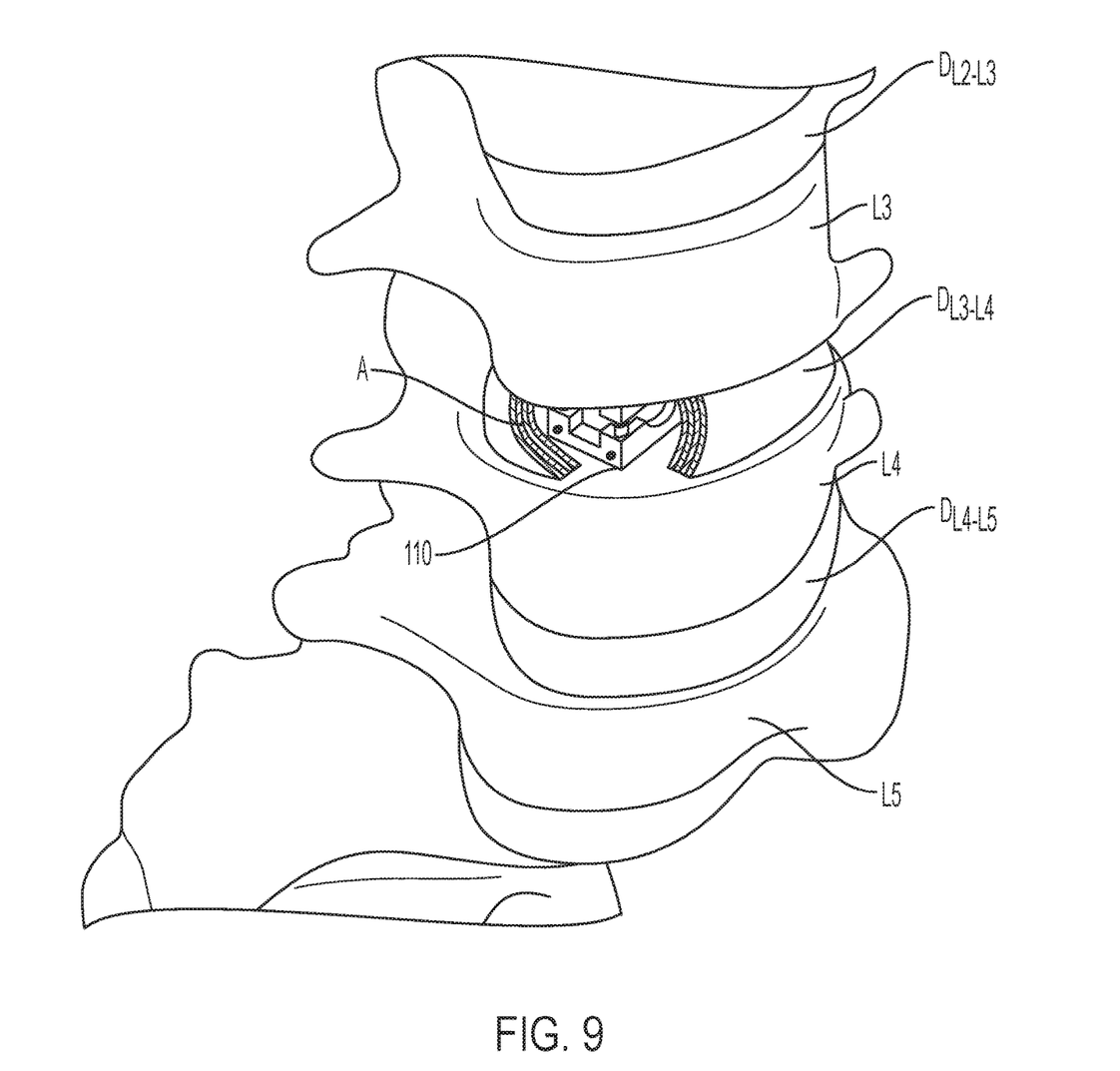

FIG. 9 is an anterior perspective view of a spinal column including expandable intervertebral fusion implant 110 in the expanded state. Expandable intervertebral fusion implant 110 is inserted into the spinal column between, for example, vertebra L3 and vertebra L4, or where disc $D_{L3-L4}$ should be. Expandable intervertebral fusion implant 110 is then vertically expanded until the desired height is reached. As previously described, expandable intervertebral implant 110 is expanded by rotating worm 200A and/or worm 200B. It should be appreciated that expandable intervertebral implant 110 may be expanded prior to insertion, or after insertion. Expandable intervertebral implant 110 is then filled with fusion material and left in situ.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Spinal column
12 Ligament
C1-C7 Cervical vertebrae
T1-T12 Thoracic vertebrae
L1-L5 Lumbar vertebrae
S Sacrum
C Coccyx
$D_{L1-L2}$ Disc
$D_{L2-L3}$ Disc
$D_{L3-L4}$ Disc
$D_{L4-L5}$ Disc
F Facet
FJ Facet joint
SP Spinous process
TP Transverse process
IF Intervertebral foramen
NC Neural canal
A Annulus
N Nucleus
DH Disc space height
110 Expandable intervertebral fusion implant
120 Inferior component
121 Hole
122 Surface
124 Surface
126 End
128 End
130A Hole
130B Hole
132A Hole
132B Hole
134A Section
134B Section
136 Tongue
138 Hole
138A Portion
138B Portion
140 Hole 142 Hole
144 Surface
146 Hole
148 Surface
150 Socket
160 Superior component
161 Hole
162 Surface
164 Surface
166 End
168 End
170A Hole
170B Hole
172A Hole
172B Hole
174A Groove
174B Groove
176 Channel
178 Hole
178A Portion
178B Portion
180 Hole
182 Hole
184 Surface
186 Socket
188 Hole
190 Surface
200A Worm
200B Worm
202A End
202B End
204A End and/or head
204B End and/or head
206A Threading
206B Threading
208A Threading
208B Threading
220A Shaft or rack
220B Shaft or rack
222A End
222B End
224A End
224B End
226A Ball
226B Ball
228A Teeth
228B Teeth
230A Teeth
230B Teeth
240A Sheath
240B Sheath
D1 Direction
D2 Direction
D3 Direction
D4 Direction
D5 Direction
D6 Direction
CD1 Circumferential direction
CD2 Circumferential direction

What is claimed is:

1. An expandable intervertebral fusion implant, comprising:
an inferior component, including:
a first top surface;
a first bottom surface;
a first end;
a second end; and,
a first hole including a first portion and a second portion;
a superior component, including:
a second top surface;
a second bottom surface;
a third end; and,
a fourth end; and,
an expansion mechanism including a flexible shaft arranged in the first hole, the flexible shaft including:
a fifth end;
a sixth end connected to the first second bottom surface; and,
a first plurality of teeth;
wherein when the expansion mechanism is displaced in a first direction with respect to the inferior component, the superior component is displaced in a second direction with respect to the inferior component, the second direction being different than the first direction.

2. The expandable intervertebral fusion implant as recited in claim 1, wherein the inferior component further comprises:
a second hole arranged adjacent to the first hole; and,
a worm comprising threading, the threading being engaged with the first plurality of teeth.

3. The expandable intervertebral fusion implant as recited in claim 2, wherein when the worm is rotated in a first circumferential direction, the flexible shaft is displaced in the first direction and the superior component is displaced in the second direction relative to the inferior component.

4. The expandable intervertebral fusion implant as recited in claim 3, wherein the first direction is perpendicular to the second direction.

5. The expandable intervertebral fusion implant as recited in claim 1, wherein the sixth end is pivotably connected to the second bottom surface.

6. The expandable intervertebral fusion implant as recited in claim 1, wherein the first portion is perpendicular to the second portion, and the flexible shaft is arranged in both the first portion and the second portion.

7. The expandable intervertebral fusion implant as recited in claim 1, wherein the flexible shaft comprises nickel titanium.

8. The expandable intervertebral fusion implant as recited in claim 1, further comprising a sheath arranged around the flexible shaft proximate the sixth end.

9. The expandable intervertebral fusion implant as recited in claim 8, wherein the sheath is connected to the second bottom surface and the first top surface.

10. The expandable intervertebral fusion implant as recited in claim 8, wherein the sheath comprises a plurality of telescoping members.

11. The expandable intervertebral fusion implant as recited in claim 1, further comprising a section extending from one of the inferior component and the superior component and a groove arranged in the other of the inferior component and the superior component, the section being engaged with the groove.

12. An expandable intervertebral fusion implant, comprising:
an inferior component, including:
a first top surface;
a first bottom surface;
a first end;
a second end; and,
a first hole including a first portion and a second portion;
a superior component, including:

a second top surface;
a second bottom surface;
a third end;
a fourth end; and,
a second hole including a third portion and a fourth portion;
a first flexible shaft arranged in the first hole, the first flexible shaft including:
a fifth end;
a sixth end connected to the second bottom surface; and,
a first plurality of teeth;
a second flexible shaft arranged in the second hole, the second flexible shaft including:
a seventh end;
an eighth end connected to the first top surface; and,
a second plurality of teeth.

13. The expandable intervertebral fusion implant as recited in claim 12, wherein the inferior component further comprises:
a third hole arranged adjacent to the first hole; and,
a first worm comprising first threading, the first threading being engaged with the first plurality of teeth.

14. The expandable intervertebral fusion implant as recited in claim 13, wherein when the first worm is rotated in a first circumferential direction, the first flexible shaft is displaced in a first direction and the superior component is displaced in a second direction relative to the inferior component, the first direction being different than the second direction.

15. The expandable intervertebral fusion implant as recited in claim 13, wherein the superior component further comprises:
a fourth hole arranged adjacent to the second hole; and,
a second worm comprising second threading, the second threading being engaged with the second plurality of teeth.

16. The expandable intervertebral fusion implant as recited in claim 15, wherein when the second worm is rotated in a first circumferential direction, the first flexible shaft is displaced in a first direction and the inferior component is displaced in a second direction relative to the superior component, the first direction being different than the second direction.

17. The expandable intervertebral fusion implant as recited in claim 12, wherein:
the first portion is not aligned with the second portion and the first flexible shaft is arranged in both the first portion and the second portion; and,
the third portion is not aligned with the fourth portion and the second flexible shaft is arranged in both the third portion and the fourth portion.

18. The expandable intervertebral fusion implant as recited in claim 12, further comprising a sheath arranged around the first flexible shaft proximate the sixth end, the sheath being fixedly secured to the second bottom surface and the first top surface.

19. The expandable intervertebral fusion implant as recited in claim 18, wherein the sheath comprises a plurality of telescoping members.

20. An expandable intervertebral fusion implant, comprising:
an inferior component including a hole arranged therein, the hole including a first portion and a second portion, the second portion being unaligned with the first portion;
a superior component displaceable relative to the inferior component;
a flexible shaft slidably engaged in the first portion and the second portion of the hole, the flexible shaft including:
a first end;
a second end pivotably connected to the superior component; and,
a plurality of teeth; and,
a worm arranged in the inferior component, the worm including threading engaged with the plurality of teeth.

* * * * *